US012585339B2

(12) United States Patent
Wegner et al.

(10) Patent No.:  US 12,585,339 B2
(45) Date of Patent:  Mar. 24, 2026

(54) SURGICAL INPUT DEVICE, SYSTEM AND METHOD

(71) Applicant: Stryker European Operations Limited, Carrigtwohill (IE)

(72) Inventors: Ingmar Wegner, Waldkirch (DE); Mukul Kashmira, Haldwani (IN); Rachana Gupta, Guwahati (IN)

(73) Assignee: Stryker European Operations Limited, Carrigtwohill (IE)

( * ) Notice: Subject to any disclaimer, the term of this patent is extended or adjusted under 35 U.S.C. 154(b) by 303 days.

(21) Appl. No.: 18/225,962

(22) Filed: Jul. 25, 2023

(65) Prior Publication Data

US 2024/0024043 A1     Jan. 25, 2024

(30) Foreign Application Priority Data

Jul. 25, 2022  (EP) .................................... 22186603

(51) Int. Cl.
| | |
|---|---|
| *G06F 3/03* | (2006.01) |
| *A61B 90/92* | (2016.01) |
| *G06F 3/0346* | (2013.01) |
| *G06F 3/0362* | (2013.01) |
| *A61B 34/20* | (2016.01) |
| *A61B 90/00* | (2016.01) |

(52) U.S. Cl.
CPC ............ *G06F 3/0312* (2013.01); *A61B 90/92* (2016.02); *G06F 3/0346* (2013.01); *G06F 3/0362* (2013.01); *A61B 2034/2055* (2016.02); *A61B 2090/3937* (2016.02)

(58) Field of Classification Search
USPC ........................................................ 345/184
See application file for complete search history.

(56) References Cited

U.S. PATENT DOCUMENTS

| | | | |
|---|---|---|---|
| 7,302,355 | B2 | 11/2007 | Jansen et al. |
| 7,643,862 | B2 | 1/2010 | Schoenefeld |
| 7,670,345 | B2 | 3/2010 | Plassky et al. |
| (Continued) | | | |

FOREIGN PATENT DOCUMENTS

| | | |
|---|---|---|
| EP | 1690503 A1 | 8/2006 |
| EP | 1990021 A1 | 11/2008 |
| (Continued) | | |

OTHER PUBLICATIONS

English language abstract for EP 1 690 503 A1 extracted from espacenet.com database on Jul. 26, 2023, 2 pages.

(Continued)

*Primary Examiner* — James Kish
(74) *Attorney, Agent, or Firm* — Howard & Howard Attorneys PLLC

(57) ABSTRACT

A surgical input device configured to enable manual user input to a remote computing system is described. In one example, the surgical input device comprises an interface configured to be attachable to a surgical object such as a patient bone. The surgical input device further comprises a manually operable input wheel infinitely rotatable relative to the interface. The input wheel defines an optically detectable wheel marking. In some variants, the surgical input device or surgical object may comprise one or more tracking elements and may thus function as a surgical tracker.

19 Claims, 10 Drawing Sheets

(56)  References Cited

U.S. PATENT DOCUMENTS

| | | | |
|---|---|---|---|
| 10,349,986 B2 | 7/2019 | Wall et al. | |
| 2001/0050673 A1 * | 12/2001 | Davenport | G06F 3/03543 |
| | | | 345/163 |
| 2002/0010479 A1 | 1/2002 | Skakoon et al. | |
| 2008/0281989 A1 | 11/2008 | Hager et al. | |
| 2015/0360019 A1 | 12/2015 | Clancy et al. | |
| 2017/0056115 A1 | 3/2017 | Corndorf et al. | |
| 2018/0271511 A1 | 9/2018 | Stanton | |
| 2020/0170712 A1 | 6/2020 | Scholl et al. | |
| 2021/0145524 A1 | 5/2021 | Akhlaghpour | |
| 2022/0175550 A1 | 6/2022 | Hughes | |

FOREIGN PATENT DOCUMENTS

| | | | | | |
|---|---|---|---|---|---|
| EP | 2977864 A1 * | 1/2016 | | ......... | G06F 3/04162 |
| EP | 3032456 B1 | 4/2018 | | | |
| EP | 3893239 A1 | 10/2021 | | | |

OTHER PUBLICATIONS

English language abstract for EP 1 990 021 A1 extracted from espacenet.com database on Jul. 26, 2023, 2 pages.
Wikipedia, "Computer Mouse", https://en.wikipedia.org/w/index.php?title=Computer_mouse&01did=1099790359, Jul. 22, 2022, 36 pages.
Wikipedia, "Disc Parking", https://en.wikipedia.org/w/index.php?title=Disc_parking&01did=1096712628, Jul. 6, 2022, 9 pages.

* cited by examiner

100

102   Receive first image data representative of a wheel marking

104   Determine, based on the first image data, a change of the wheel marking caused by rotation of or translation of input wheel 106   Determine a user input associated with the change of the wheel marking 108   Interpret the first user input as a command

SURGICAL INPUT DEVICE, SYSTEM AND METHOD

PRIORITY CLAIM

This application claims priority under 35 U.S.C. § 119 to European Patent Application No. 22186603.1, filed Jul. 25, 2022, the entire contents of which are hereby incorporated by reference herein.

TECHNICAL FIELD

The present disclosure generally relates to computer-assisted surgery. In particular, a surgical input device configured to enable manual user input to a remote computing system is provided. Also provided are a surgical input system comprising the surgical input device, a method for determining a manual user input at the surgical input device, and a computer program product.

Background

In recent decades, computer-assisted techniques have widely been used to assist surgeons in performing surgical procedures such as spinal surgery, joint replacement surgery and neural surgery. During such surgical procedures, a surgeon may need to perform a user input at a computing system. For example, the surgeon may wish to confirm a parameter suggested by the computer system or may wish to select an item from a list offered by the computer system on a display device.

A conventional input device such as a keyboard, touchscreen or computer mouse will typically be located at a certain distance from the operating table in order not to interfere with the surgeon's surgical activities at a patient. This means, however, that the surgeon has to turn away from the patient to perform an input operation at the computer system via such an input device. Furthermore, conventional input devices may not be sterile. Therefore, the use of a conventional input device may require the surgeon to disinfect his or her hands after having interacted with the input device. The use of conventional input devices thus tends to increase the duration of a surgical intervention.

In EP 3 893 239 A1 it is suggested to use voice commands for a remote control of a computer system in the operating room. Voice commands avoid some of the issues associated with conventional input devices. In certain situations, however, the use of voice commands may not be as intuitive to a surgeon as, for example, the use of a conventional input device such as a computer mouse.

Anonymous: "Disc parking—Wikipedia", 6 Jul. 2022 (2022-07-06), pages 1-9, discloses different parking disks, e.g., a European standard parking disk.

US 2008/281989 A1 discloses a medical instrument having a control device for controlling medical treatment software, wherein the control device includes a transmitter for transmitting software control signals and at least one control for activating the transmitter.

US 2022/175550 A1 discloses a technique for minimally invasive use of robotic appendage for surgery.

US 2018/271511 A1 discloses an end effector for a robotic-assisted surgical system having an adjustable inner diameter.

US 2017/056115 A1 discloses a method that includes receiving, by a first device including a processor, image data associated with an external portion of a tool located within a body of a patient, wherein the image data includes first information indicative of a first fiducial marker on the external portion of the tool. The method also includes determining one or more relative positions of an internal portion of the tool within the body relative to one or more anatomical structures of the body based on the image data and a defined configuration of the tool. The method also includes generating one or more representations of the tool within the body relative to the one or more anatomical structures based on the one or more relative positions and the defined configuration of the tool.

US 2015/360019 A1 discloses a fiducial deployment system with a handle configured for actuation of same. The handle includes an actuation mechanism with a collet and plunger actuation member configured for incrementally or otherwise controllably deploy one or more fiducials at a time by advancing a stylet through and/or retracting the body of a slotted needle in which fiducials are disposed with a fiducial protrusion extending into the needle slot, which also includes retaining structures that do not impede the needle lumen.

Anonymous: "Computer mouse—Wikipedia", 22 Jul. 2022 (2022-07-22), pages 1-36, discloses different examples for mechanical, opto-mechanical and optical computer mice.

SUMMARY

There is a need for a surgical input device that solves one or more of the aforementioned or other problems.

According to a first aspect, a surgical input device is provided that is configured to enable manual user input to a remote computing system. The surgical input device comprises an interface configured to be attachable to a surgical object and a manually operable input wheel infinitely rotatable relative to the interface, wherein the input wheel defines an optically detectable wheel marking.

The computer system may be remote relative to the surgical object to which the surgical input device is to be attached. The surgical input device may not comprise an electrical connector or cable for a wired connection to the computer system. The surgical input device may thus operate as a wireless remote control for the computer system. The surgical input device may be a fully passive device in that it does not consume any electric power.

The surgical object may be a patient (e.g., a bone of a patient, such as the patient's spine or femur), a surgical instrument or a surgical auxiliary device (e.g., an operating table). In some variants, the surgical input device is integrated into a surgical auxiliary device (e.g., in a surgical tracker or a field generator for electromagnetic tracking). In such variants, the interface for the surgical input device may be provided by the surgical auxiliary device.

The input wheel may have a smooth or non-smooth outer contour. For example, the wheel may take the form of a rotatable cylinder with a smooth or serrated outer contour. In other variants, the wheel may take the form of a rotatable star with a number of spikes. In still other variants, the wheel may have a polygonal cross-section in a plane perpendicular to its axis of rotation.

The wheel marking may be optically detectable at a distance (e.g., of one or more meters) from the surgical input device. The wheel marking may be configured to be detectable by an optical camera. The wheel marking may have a two-dimensional or a three-dimensional configuration, or may be combined two-/three-dimensional feature. An exemplary three-dimensional wheel marking can be realized by a spike of a star-shaped input wheel.

The wheel marking may comprise at least one of one or more light reflecting elements and one or more light emitting elements (e.g., at least one light emitting diode, LED). The wheel marking may be detectable in the visible spectrum. The wheel marking may comprise at least one of a coloured substrate and a printing.

The wheel marking may change in a circumferential direction of the input wheel. Additionally, or in the alternative, the wheel marking may change in a radial direction of the input wheel.

The wheel marking may take the form of one or more colours. Additionally, or in the alternative, the wheel marking may take the form of one or more geometric shapes (e.g., it may take the form of at least one geometric pattern or the form of at least one letter, number or other character).

The wheel marking may comprise at least an optically detectable first characteristic and an optically detectable second characteristic which are offset relative to each other in the circumferential direction of the input wheel. The first and second characteristics may be different from each other. The first and second characteristics may comprise at least one of different colours and different geometric shapes.

At least one of the first and second characteristics may comprise a uniform colour such as red, blue, green, yellow, orange or purple. The wheel marking may comprise at least one colour gradient between the first and second characteristics. The wheel marking may comprise more than two optically detectable characteristics offset relative to each other in the circumferential direction of the input wheel, wherein all or at least a subset of the characteristics are different from each other.

The surgical input element may comprise an occlusion element configured to cover a portion of a rotational trajectory of the wheel marking. The input wheel may be rotatable relative to the occlusion element. The occlusion element may cover between 5% to 95% of the rotational trajectory of the wheel marking (such as more than 10%, 25%, 50%, 66%, or more than 87.5%). A portion of the input wheel not covered by the occlusion element may at least essentially have the shape of a circular sector. The circular sector may have a central angle of more than 45°, 90°, 135°, 180°, or more than 270°. The occlusion element may have a first opening that is dimensioned at least essentially in the same size or smaller than one of the first and second characteristics.

The surgical input device may comprise a manually operable input button movable between a first position and at least one second position. A transition of the input button between the first position and the second or a third position may be optically detectable. The input button may be configured to move in a translatory manner. The first and second positions of the input button may be positions located at opposite ends of a translation range. The input button may be biased towards the first position. The surgical input device may comprise at least one piston with a spring that biases the input button towards the first position. The input button may be movable between three, four, five, or more discrete positions.

The surgical input device may comprise an optically detectable button-related marking. In such a case, the transition between the first position and the at least one second or a third position may change an optical visibility of the button-related marking. The occlusion element may be movable with the input button. The occlusion element may be integrally formed with the input button. Alternatively, or in addition, the occlusion element may constitute the input button. The occlusion element may have a second opening that, upon the transition of the input button between the first position and the at least one second or a third position, can selectively be brought in and out of alignment with the button-related marking. In this manner, the optical visibility of the button-related marking can be changed.

The button-related marking may be arranged on a surface of the input wheel. The button-related marking may be arranged at an outer edge of a side surface of the input wheel. The button-related marking may be arranged on a hub of the input wheel. Additionally or alternatively, the button-related marking may comprise at least one optically detectable marker on the input button (e.g., on a piston comprised by the input button).

The input button and the input wheel may be arranged relative to each other so as to permit a one-hand operation of both the input button and the input wheel. The input button may have a button surface for manually engaging the input button and the input wheel may have a wheel engagement surface for manually engaging the input wheel. In some variants, the button surface and the wheel engagement surface are arranged adjacent to each other. The button surface may be arranged flush or elevated relative to the wheel engagement surface.

The wheel marking may be arranged on at least one of a side face of the input wheel and an outer rim surface of the input wheel. The wheel marking may be arranged on one or both side faces of the input wheel. In such a case, the occlusion element, if present, may also be arranged on both side faces of the input wheel. Characteristics of the wheel marking on the outer rim surface of the input wheel adjacent to characteristics of the wheel marking on the side face of the input wheel may be identical (e.g., the same colour) or at least similar (e.g., the same shape but with a different size and/or orientation).

A rotatability of the input wheel may be continuous or may be divided into discrete increments. The rotatability may, for example, be divided into a number of increments in a range between three and thirty six (e.g., four, five, six, twelve, or 24). The number of increments may be identical to or an integer multiple of the number or characteristics of the wheel marking.

The surgical input device may comprise at least one tracking element configured to be detectable by a tracking system. In such a variant, the interface of the surgical input device may be attached to the surgical object (e.g., a patient, a surgical instrument or a surgical auxiliary device) so that the surgical object becomes trackable by the tracking system.

At least the input wheel (optionally together with the occlusion element and/or the input button) may be detachable from remainder of the surgical input device such as from the interface. In some cases, the interface may be an integral part of a surgical tracker comprising the at least one tracking element and may also serve for attaching the input wheel (optionally together with the occlusion element and/or input button) to the surgical object. In this variant, the input wheel (optionally together with the occlusion element and/or input button) may be detachable from the surgical tracker and, thus, from the interface. In this or another variant, the at least one tracking element may be detachable from the surgical input device and, thus, from the interface.

The at least one tracking element may be an optically trackable element. The at least one tracking element may comprise at least one of a light reflector and a light emitter. The at least one tracking element may be configured to at least one of reflect and emit light of at least one of visible light, infrared light, and ultraviolet light. The at least one tracking element may comprise a component configured to be tracked electromagnetically, such as at least one coil. In some variants, two, three, four or more optically trackable elements may be provided. In some variants, one or two electromagnetically trackable elements may be provided.

According to a second aspect, a surgical input system is provided. The surgical input system comprises the surgical input device as described herein and an optical camera system configured to generate image data representative of at least the wheel marking. The optical camera system may be part of a tracking system configured to track one or more tracking elements (e.g., associated with one or more surgical trackers) in a field of view of the camera system. For example, the optical camera system may comprise a first (e.g., stereo) camera configured to capture (at least) infrared light and a second camera that is configured to capture (at least) visible light. The second camera may operate in the visible spectrum to detect the wheel marking and the first camera may operate in the infrared spectrum to detect the one or more tracking elements that reflect or emit infrared light.

According to a third aspect, a method implemented by at least one processor for determining a manual user input at a surgical input device to a remote computing system is provided. The surgical input device is attached to a surgical object and comprises a manually operable input wheel infinitely rotatable relative to the surgical object, wherein the input wheel defines an optically detectable wheel marking. The method comprises receiving first image data representative of the wheel marking. The method further comprises determining, based on the first image data, a change of the wheel marking caused by rotation of the input wheel. The method also comprises determining a first user input associated with the change of the wheel marking.

In some variants, the first and any further user input may not have any surgical effect on a patient to be treated or on any device for patient treatment.

The change of the wheel marking may be detected by comparing one image of the first image data to one or more subsequent images of the first image data. The change of the wheel marking caused by rotation of the input wheel may be determined from a unique signature of the rotational motion, such as by detecting a rotational trajectory of the wheel marking (e.g., of a predefined diameter) or by detecting particular characteristic (or sequence of characteristics). In some variants, the method comprises differentiating a change of the wheel marking caused by rotation of the input wheel from a change of the wheel marking caused by other actions, such as a movement of the entire surgical input device.

The method may further comprise interpreting the first user input as a command. In some variants, the command may be related to one of an incrementation and a decrementation of a parameter (e.g., at the remote computing system). In such or other variants, the command may be related to a mode change (e.g., a change of an operational mode related to a computer-assisted surgery application). In such or still other variants, the command may be related to a user confirmation (e.g., of a parameter or a setting at the remote computer system). The parameter incrementation or decrementation may relate to increasing or decreasing an operating parameter of a surgical instrument (e.g., rotational speed of a motor, a suction strength, or an extension of a translational arm), an operating parameter of a operating room (e.g., a light intensity), or an operating parameter of a tracking system (e.g., a frame rate or zoom function of a tracking camera system). The parameter incrementation or decrementation may relate to a scrolling through pages or menu items of a list displayed on a display device. The parameter incrementation or decrementation may relate to a zooming in/out operation on the display device.

The wheel marking may comprise an optically detectable first characteristic, an optically detectable second characteristic, and an optically detectable third characteristic which are offset relative to each other in the circumferential direction of the input wheel. The first, second and third characteristics may be different from each other. An occlusion element may be configured to cover a portion of a rotational trajectory of the wheel marking. In such a case, determining the change of the wheel marking may comprise determining a sequence of the first, second and third characteristics not being covered by the occlusion element.

Additionally or alternatively, determining the change of the wheel marking may comprises determining a movement of at least one characteristic based the first image data.

The surgical input device may further comprise a manually operable input button that is movable between a first position and at least one second position. In such a case, the method may further comprise determining, based on the first image data or based on second image data, a transition of the input button between the first position and the at least one second or a third position and determining a second user input associated with the determined transition.

According to a fourth aspect, a computer program product is provided. The computer program product comprises instructions that, when executed on at least one processor, cause the at least one processor to carry out any of the methods described herein. The computer program product may be stored on a non-transitory media storage such as a hard drive, a compact disc, or a USB flash drive.

BRIEF DESCRIPTION OF THE DRAWINGS

Further details, advantages and aspects of the present disclosure will become apparent from the following embodiments taken in conjunction with the drawings, wherein.

DETAILED DESCRIPTION

Figure 1:
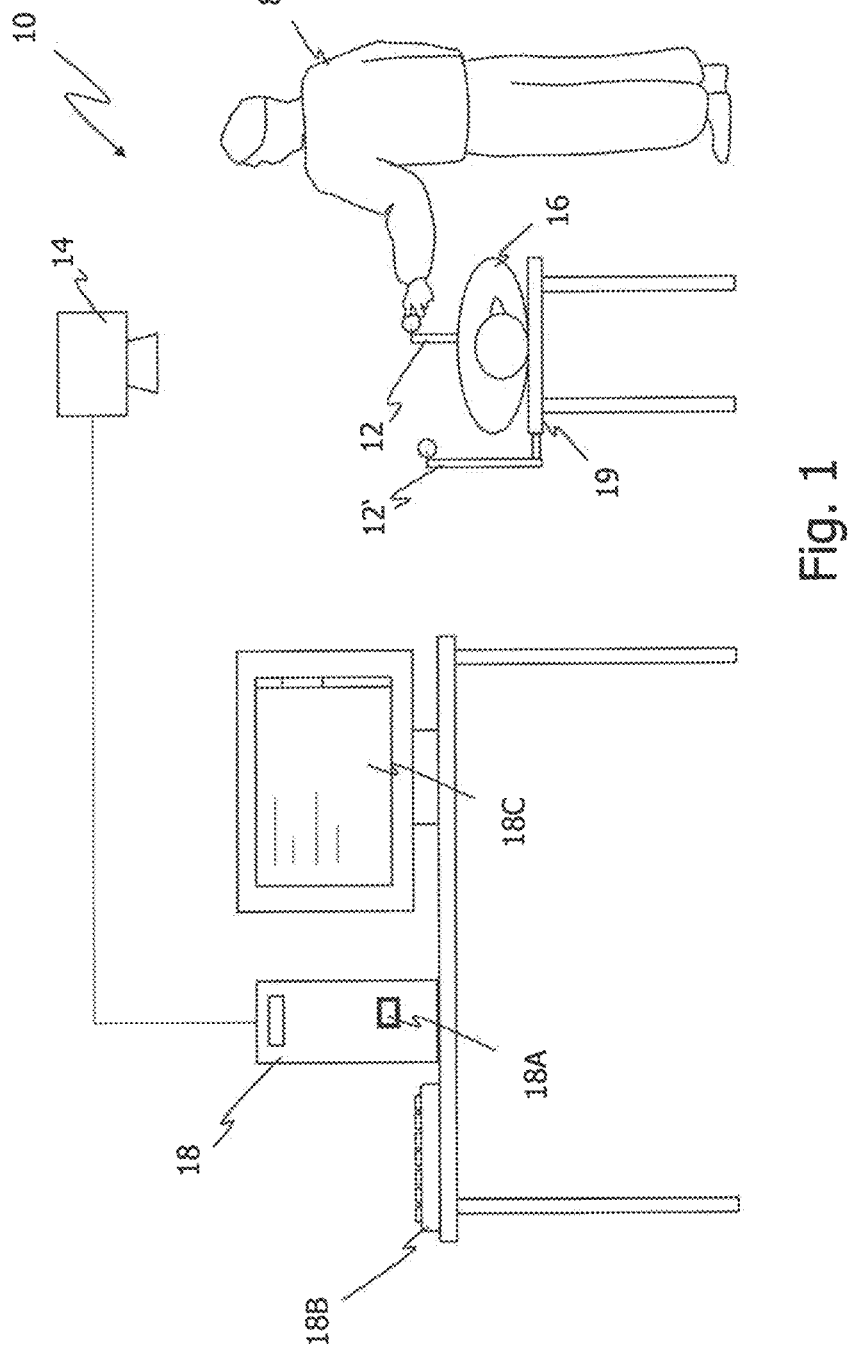
FIG. 1 shows a surgical input system with a surgical input device and an optical camera system.

In the following description, examples of a surgical input device, a surgical input system comprising the surgical input device, a computer program product, and a method for determining a manual user input at the surgical input device will be explained with reference to the drawings. The same reference numerals will be used to denote the same or similar structural features.

FIG. 1 illustrates a surgical scenario with a user 8 (e.g., a surgeon or a surgical assistant) and a surgical input system 10 configured to determine a user input by the user 8. The surgical input system 10 comprises a surgical input device 12 and an optical camera system 14. In the exemplary scenario of FIG. 1, the surgical input device 12 is attached to a patient 16 via an interface (e.g., a bone clamp or bone screw, not shown) of the surgical input device 12. Alternatively, the surgical input device 12 may be attached to any other surgical object such as a surgical instrument, a surgical robot or a surgical tracker. In this regard, FIG. 1 illustrates another surgical input device 12' attached via an interface (e.g., a screw connection, not shown in FIG. 1) to an operation table 19.

FIG. 1 further illustrates a computing system 18 configured to be operated via the surgical input system 10. The computing system 18 comprises one or more processors 18A (e.g., in the form of one or more central processing units, CPUs) that may be configured to perform method aspects of the present disclosure. The computing system 18 can be realized as a stand alone computer, a desktop, a tablet computer or by cloud computing resources. The computing system 18 further comprises an optional keyboard 18B and an optional display device 18C (e.g., a computer monitor or the screen of a tablet computer).

If the user 8 were to interact with the computing system 18 using a conventional input device such as the keyboard 18B or a computer mouse (not shown), the user 8 may risk contamination, which may require subsequent disinfection before attending to the patient 16. Furthermore, such conventional input devices may be located at a distance from the patient 16, possibly requiring the user 8 to interrupt a surgical procedure and walk over or turn to the input device for controlling the computing system 18. These issues are addressed by the surgical input device 12.

The surgical input device 12 is attached to a surgical object such as the patient 16 and, thus, can easily be operated by the user 8 without having to walk over or turn to the computing system 18. The surgical input device 12 thus enables a remote control of the computing system 18 from the surgical site. The surgical input device 12 can easily be detached via its interface from the surgical object for sterilization purposes. The user 8 can therefore manually interact with the sterile surgical input device 12 without having to clean his or her hands afterwards (e.g., hand antisepsis).

Figures 2A, 2B, 2C:
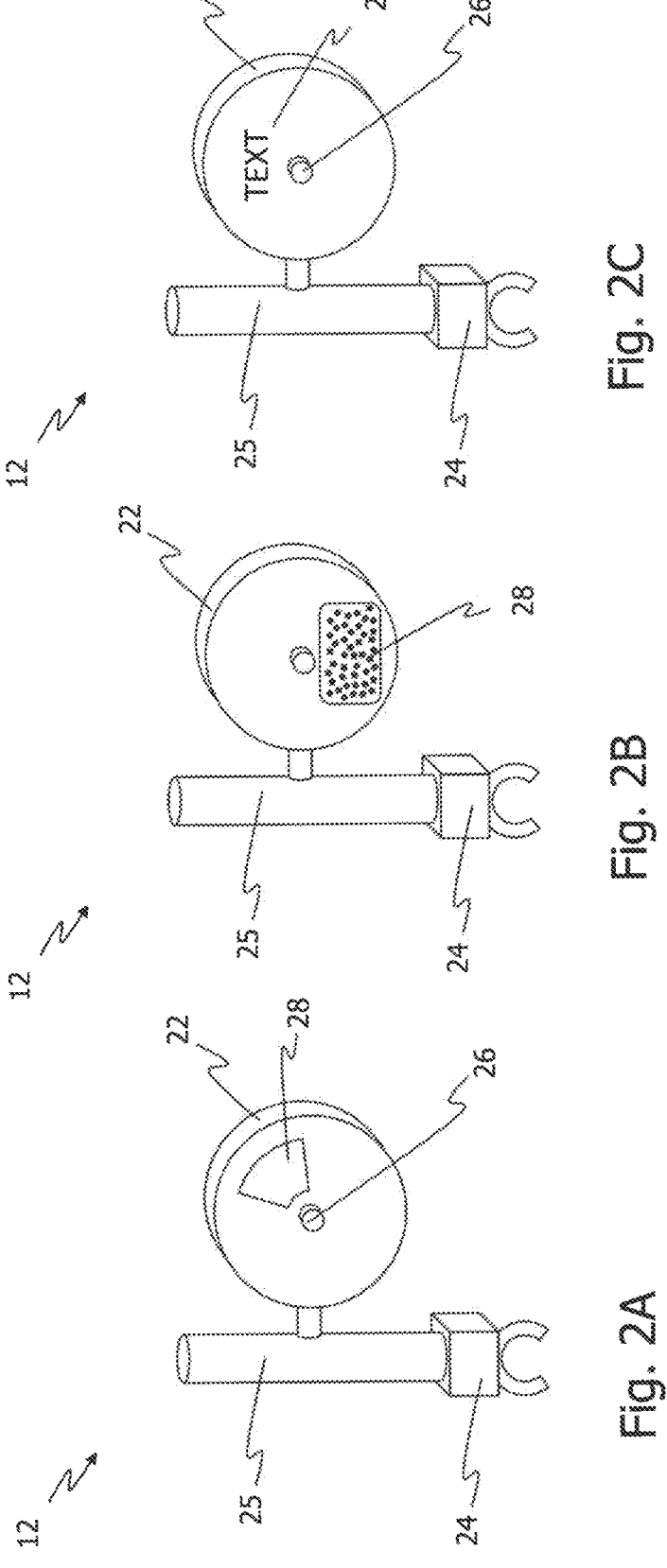
FIGS. 2A-C show examples of a surgical input device with different optically detectable wheel markings.

FIG. 2A shows a first example of a surgical input device 12. The surgical input device 12 comprises a manually operable input wheel 22 and an interface 24 configured to be attached to the surgical object (e.g., the patient 16 or the operating table 19 in FIG. 1). The interface 24 depicted in FIG. 2A comprises a clamp, e.g., for clamping around a cylindrical part of the surgical object (e.g., around a cylindrical housing of a surgical instrument or around a bone portion). Alternatively or additionally, the interface 24 may comprise at least one of an adhesive, a screw-type connection, a magnet, a wire loop, and so on.

The input wheel 22 is configured to enable manual user input to the computing system 18. In more detail, the input wheel 22 is configured to be rotated using one or more of the user's fingers, in particular in a way similar to a mouse wheel. To this end, one or more other fingers of the user 8 may rest on a shaft 25 or another structure connecting the input wheel 22 with the interface 24. The input wheel 22 may be realized in the form of a short cylinder, as illustrated in FIG. 2A, with smooth surfaces. In other variants, the input wheel 22 may have a different appearance (e.g., at least partially spherical, star-shaped or with a polygonal cross-section, such as in the form of an octagon).

In the variant illustrated in FIG. 2A, the manually operable input wheel 22 is infinitely rotatable relative to the interface 24 around a wheel axis 26. As a result, the input wheel 22 can be rotated in at least one direction for an unlimited amount of rotations. In other variants, the input wheel 22 is rotatable over an angular range of less then 360° (e.g., over less than 270°, 180° or less than 90°). To this end, one or more stops may be provided that limit rotatability of the input wheel 22 to a predefined angular range. While the input wheel 22 shown in FIG. 2A is mounted on an axis 26, the input wheel 22 may in alternative configurations be arranged in a housing, wherein the input wheel 22 is able to rotate by sliding along an inside surface of the housing.

The input wheel 22 illustrated in FIG. 2A is rotatable in two opposite rotational directions. Alternatively, the input wheel 22 may be rotatable in only one direction but blocked in the other (e.g., by a clutch).

Rotatability of the input wheel 22 may be realized continuously or may be divided into discrete increments. To this end, the input wheel 22 may comprise a detent or protrusion cooperating with a corresponding stationary feature (not illustrated) that repeatedly resists (without fully blocking) rotation of the input wheel 22. As a result, the user 8 may have a tactile feedback of the rotation of the input wheel 22. Each rotational increment may correspond to a dedicated user input. The rotation of the input wheel 22 may be divided into discrete increments in a range of 1 to 120°, e.g., 3°, 22.5°, 45°, 60°, or 90°.

As shown in FIG. 2A, the input wheel 22 has an optically detectable wheel marking 28. The wheel marking 28 may be an active (i.e., light emitting) or a passive (i.e., light reflecting) component. The camera system 14 is configured to capture the wheel marking 28 in corresponding image data. As such, there is no need for a wired connection to the computer system 18 for controlling same. Moreover, the surgical input device 12 does not consume any electric power (at least in variants in which the wheel marking 28 is realized as a passive component).

Since the wheel marking 28 is optically detectable, the camera system 14 can detect a change of the wheel marking 28 specifically resulting from a rotation of the input wheel 22 (other wheel marking changes may not be of interest and may need to be filtered out, for example using image processing techniques). The corresponding change of the wheel marking 28 may in same implementations be detected relative to any stationary component in a field of view of the camera system 14, such as relative to another marking on the shaft 25 or elsewhere on the surgical input device 12. The detected change of the wheel marking 28 can be translated (e.g., by the computer system 18 to which the camera system 14 is communicatively attached) into a user input as will be described below with reference to FIG. 3.

The wheel marking 28 can be of any type detectable by the camera system 14. The wheel marking 28 may, for example, comprise a geometric structure being optically (e.g., in terms of a colour) differentiated from the remainder of the input wheel 22 (see FIG. 2A), a geometric shape (see the geometric pattern of FIG. 2B) or a text (see FIG. 2C). The wheel marking 28 can be two-dimensional or three-dimensional, or a combination thereof.

In some variants, the wheel marking 28 is visually detectable by the user 8. In such variants, the user 8 can visually check and confirm operation of the input wheel 22. In other variants, the wheel marking 28 may be detectable only in the infrared spectrum.

Figure 2E:
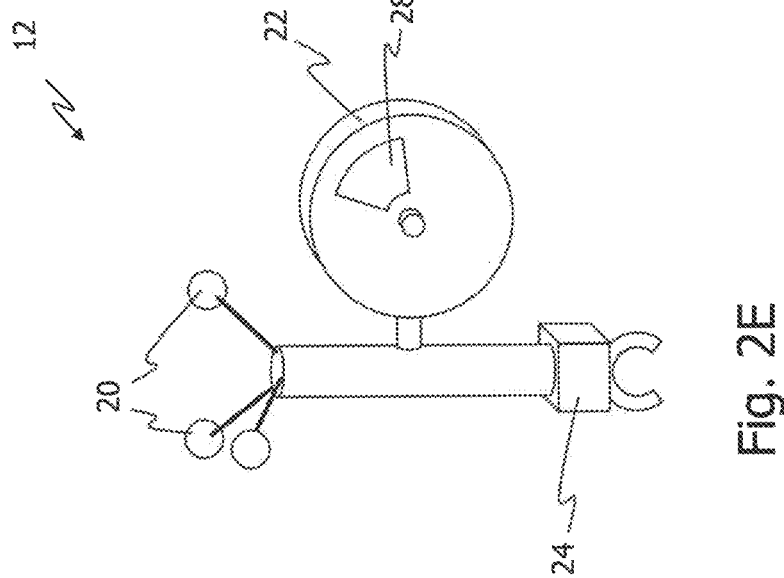
FIG. 2E shows another example of a surgical tracker comprising the surgical input device and multiple tracking elements.
Figure 2D:
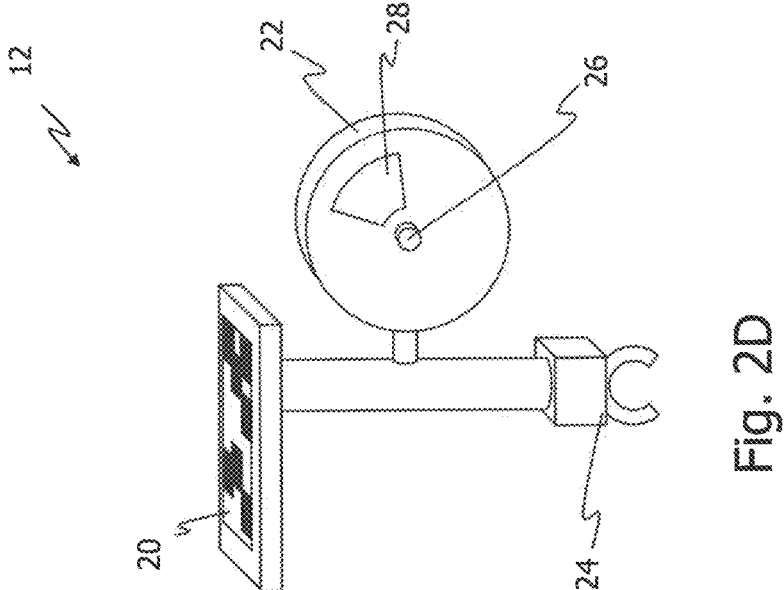
FIG. 2D shows an example of a surgical tracker comprising the surgical input device and a single tracking element.

FIG. 2D shows another example of a surgical input device 12 carrying a tracking element 20 configured to be detectable by a surgical tracking system. The tracking system may be an optical tracking system. In such a case, the optical camera system 14 of FIG. 1 may be part of, or constitute, the optical tracking system. However, the tracking system and the tracking element 20 detectable by the tracking system may use any other tracking technology such as electromagnetic tracking and time-of-flight tracking. The surgical input device 12 depicted in FIG. 2D has a single tracking element 20 with a visible pattern (e.g., a QR code) that allows determining one or both of a position and orientation of the tracking element 20 and, consequently, of the surgical input device 12 in a tracking coordinate system.

FIG. 2E shows a further example of a surgical input device 12 with multiple tracking elements 20. The tracking elements 20 depicted in FIG. 2E are passive markers in the exemplary form of spheres. The tracking elements 20 may predominantly reflect light in a specific spectrum, such as at least one of infrared light, visible light, and ultraviolet light. The surgical input device 12 shown in FIG. 2E has three tracking elements 20, which allows tracking the surgical input device 12 six degrees of freedom. Alternatively, the surgical input device 12 may have two, four, five, or more tracking elements 20.

In other variants, one or more or all of the tracking elements 20 illustrated in FIG. 2E may be active tracking elements. As such, at least one of the tracking elements 20 may comprise a light emitter such as a light emitting diode.

In the scenarios of FIGS. 2D and 2E, and in similar tracking-related scenarios, the device 12 may also be considered to constitute a surgical tracker with user input capabilities resulting from the provision of the input wheel 22.

The optical camera system 14 that captures the wheel marking 28 may, but does not necessarily have to be a part of the tracking system that tracks the one or more tracking elements 20. For example, the one or more tracking elements 20 may reflect or emit infrared light and the wheel marking 28 may reflect or emit visible light. In such a case, it is sufficient for the optical camera system 14 to detect visible light, and a dedicated tracking camera system can be provided to detect infrared light for tracking the one or more tracking elements 20. Both camera systems may be integrated into a single camera unit. Alternatively, a single camera system (or single camera) may be provided that can detect visible light and infrared light and can therefore detect (and track) the one or more tracking elements 20 and the wheel marking 28 simultaneously. Further alternatively, the one or more tracking elements 20 and the wheel marking 28 may be detectable in a similar or the same spectrum (e.g., both detectable in the visible spectrum or in the infrared spectrum). In such a case, a single camera system (or single camera) may be used.

At least the input wheel 22 may be detachable from a remainder of the surgical input device 12. The remainder may comprise at least the interface 24 and, optionally, the one or more tracking elements 20. The surgical input device 12 may comprise a snap-in connector or other connecting structure configured to releasably engage the input wheel 22. Such a configuration is particularly useful if the interface 24 and the one or more tracking elements 20 form an integral part of a surgical tracker. Therefore, the input wheel 22 can be attached to the surgical tracker if the user intends to issue user inputs, and the input wheel 22 can be removed to reduce the size and weight of the surgical tracker or for sterilization purposes. In such or other variants, the one or more tracking elements 20 may be detachable from the remainder of surgical input device 12. The remainder may comprise at least the interface 24 and the input wheel 22.

Figure 3:
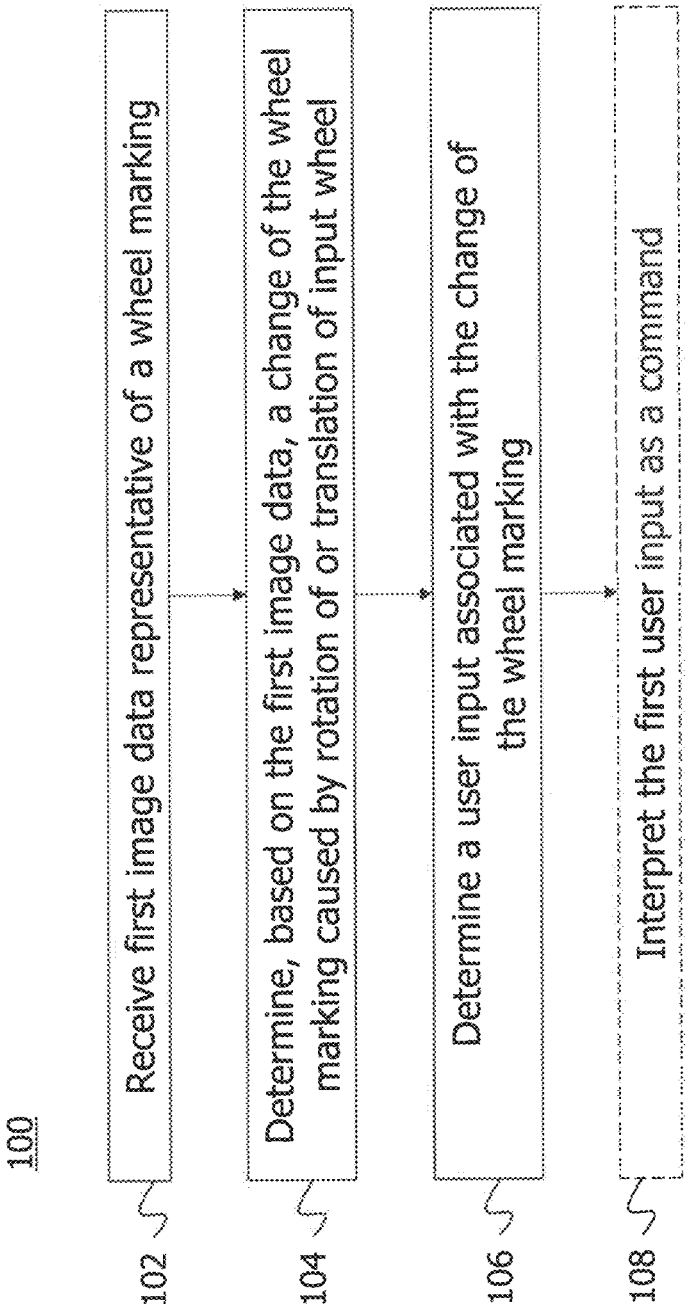
FIG. 3 shows a flow diagram of a method for determining a manual user input by a surgical input device to a remote computing system.

FIG. 3 shows a flow diagram 100 of a method for determining a manual user input at the surgical input device 12 (e.g., according to any of FIGS. 2A to 2E) to the remote computing system 18 of FIG. 1. The method steps may be performed by the computing system 18 itself that is communicatively coupled to the camera system 14. In other variants, the method steps are least partially performed by another computer system communicatively coupled to both the camera system 14 and the computer system 18.

The method comprises, in step 102, receiving by the computing system 18 image data representative of the wheel marking 28. The image data are captured by the optical camera system 14. The image data may take the form of a video stream or of a sequence of images taken at a low frame rate. As such, the image data may be taken by a video camera of the optical camera system 14.

The method further comprises, in step 104, determining, by the computing system 18 and based on the image data, a change of the wheel marking 28 caused by rotation of the input wheel 22. In the example shown in FIG. 2A, rotation of the input wheel 22 will cause the wheel marking 28 to move on a predefined circular trajectory and along with the input wheel 22. Detection of this circular trajectory may thus be interpreted as the change of the wheel marking 28 (caused by rotation of the input wheel 22) that is determined in step 104. For example, the image data may comprise a temporal sequence of images (e.g., a video stream) which depict the wheel marking 28 at different rotational positions in each image. Determining the wheel marking 28 in each image and comparing the determined wheel markings 28 of each image (e.g., with respect to a predefined circular trajectory) allows determining the change of the wheel marking 28.

If necessary, supplemental information may be evaluated in step 104. For example, in case one or more tracking elements 20 are provided (see FIGS. 2D and 2E), determining the change of the wheel marking 28 may further be based on tracking information that is indicative of at least one of position and orientation of the one or more tracking elements 20. For example, if the surgical input device 12 is not stationary and moves in its entirety (e.g., in the case the surgical input device 12 is attached to a surgical instrument and the surgical instrument is moved by the user), any movement of the surgical input device 12 determined from the tracking information may be subtracted from the image data, or information derived therefrom, to determine a change of the wheel marking 28 caused by a rotation of the input wheel.

The method illustrated in FIG. 3 further comprises, in step 106, determining a user input associated with the change of the wheel marking 28 determined in step 104. In an optional step 108, the method may comprise interpreting the user input as a command. The command may relate to an ongoing computer-assisted surgical procedure under control of the computer system 18 or to any other processor-controlled procedure. The procedure controlled by the command may be different from a surgical step.

As an example, the command derived from the user input in step 108 may be related to scrolling through pages or menu items on the display device 18C or zooming in or out of a view on the display device 18C. Other examples of commands relate to changing an operating parameter of a surgical instrument (e.g., a rotational speed of a motor, a suction strength, an extension of a translational arm), an operating parameter of surgery room equipment (e.g., a light intensity), and an operating parameter of the tracking system (e.g., a frame rate or a zoom function of a tracking camera system). Of course, the command can generally be related to incrementation or decrementation of a parameter, but also to other selections, including selection of a mode change.

If the input wheel 22 is configured to be selectively rotatable in two opposite rotational directions, the user 8 may switch between parameter incrementation and parameter decrementation by selecting a certain direction of rotation. As such, the user input may depend on a rotation direction of the wheel marking 28. For example, rotation of the wheel marking 28 in a first direction may correspond to scrolling a page downwards, zooming into the view, or increasing an operating parameter, whereas rotation of the wheel marking 28 in an opposite second direction may correspond to scrolling a page upwards, zooming out of the view, or decreasing an operation parameter.

The user input may be associated with a degree of rotation of the wheel marking 28. For example, the amount of page scrolling may correspond to the degree of rotation of the wheel marking 28 (e.g., the wheel marking 28 needs to rotate 90° for scrolling an entire page). In case the rotatability of the input wheel 22 is divided into discrete increments, the user input may be associated with individually moved increments. For example, for each increment the wheel marking 28 is moved, the page is scrolled a fixed amount (e.g., 5% of a page).

The user input may be associated with a duration in which the wheel marking 28 is changing. For example, for the duration the wheel marking 28 is changing, a page is scrolled at a fixed speed independent from a rate of change of the wheel marking 28.

The method illustrated in FIG. 3 may further comprise generating an output signal that indicates to the user 8 that a command has been accepted. The output signal may be an acoustic signal or a visual signal. The output signal may be generated by the computer system 18.

The wheel marking 28 depicted in FIG. 2A comprises a single optically detectable characteristic 30 (e.g., a geometric shape of a particular colour). However, the wheel marking 28 may comprise multiple and possibly different geometric shapes and/or colours. In some variants, the number of optically detectable characteristics 30 depends on the use case and in particular on the number of selections that may need to be made. The provision of one or two optically detectable characteristics 30 may suffice for simple on/off or similar decisions to be signalled. In case a selection is to be made from a longer list, a larger number of optically detectable characteristics 30 may be provided (e.g., to limit the extent to which the wheel needs to be rotated for a desired input operation).

Figures 4A, 4B, 4C, 4D, 4E, 4F, 4G:
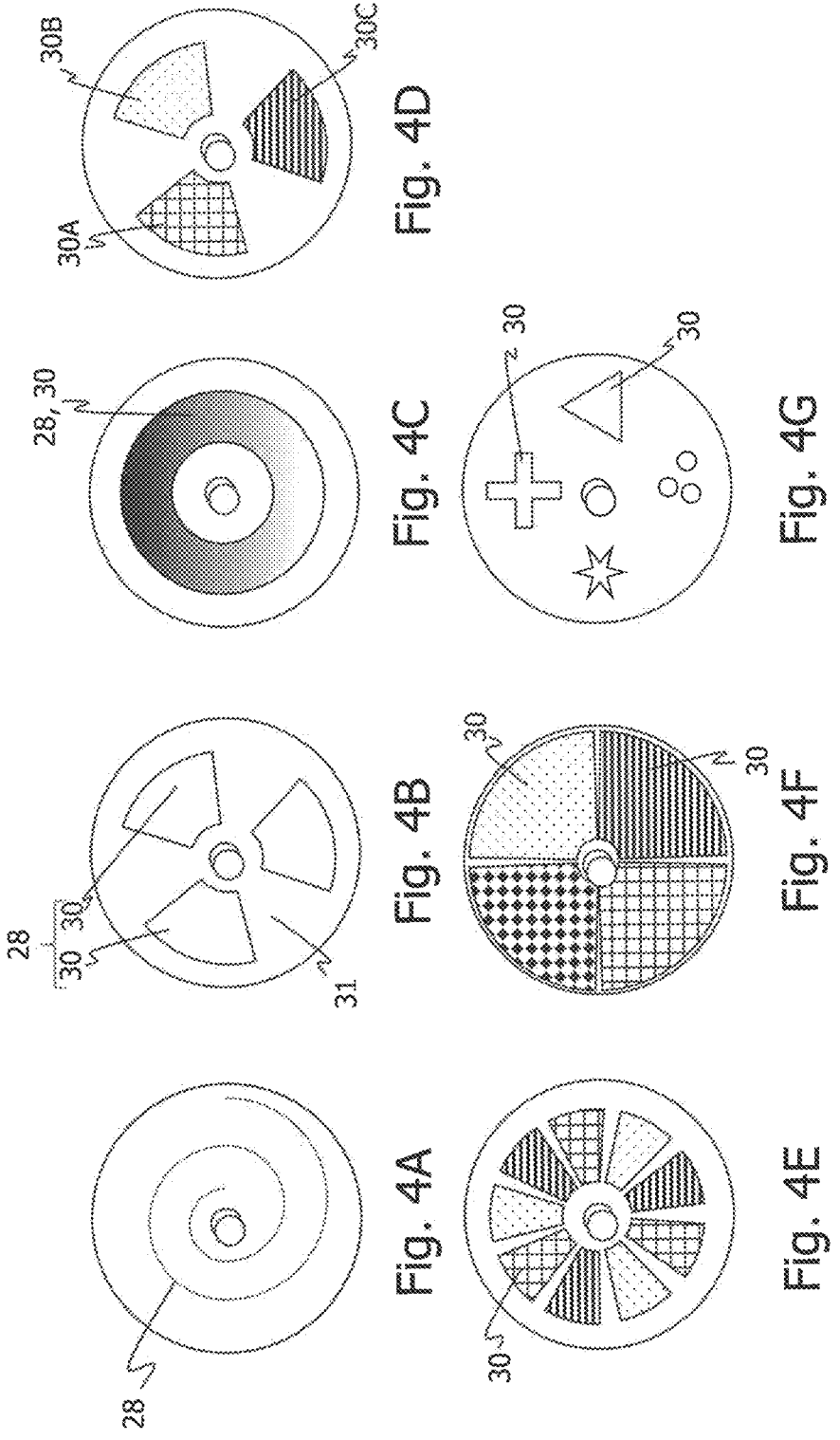
FIGS. 4A-G show a various wheel marking examples.

FIG. 4A shows a wheel marking 28 that is realized as a single optically detectable characteristic 30 in the form of a spiral. A change of the wheel marking 28 caused by a rotation of the input wheel 22 can be detected by tracking the (asymmetric) shape of the spiral or by the appearance of line segments moving radially inward or outward during rotation of the wheel marking 28.

FIG. 4B shows a second example of a wheel marking 28, wherein the wheel marking 28 comprises three optically detectable characteristics 30. The characteristics 30 may be tracked individually or as a combined pattern that comprises all the characteristics 30. The characteristics 30 may be identical. The wheel marking 28 in one variant comprises gaps 31 between the characteristics 30. The gaps 31 may be used to better differentiate the characteristics 30. The gaps may additionally or alternatively be used to determine movement of the characteristics 30. In some variants, the wheel marking 28 may have no or essentially no gaps between the characteristics 30.

The examples of wheel markings 28 depicted in FIGS. 4A and 4B can be realized with a single colour. However, the wheel marking 28 may include a plurality of colours that aid in the detection of the change of the wheel marking 28.

FIG. 4C shows a third example of a wheel marking 28 with an optically detectable characteristic 30 that gradually changes colour in a rotation direction of the input wheel 22. The characteristic 30 shown in FIG. 4C changes between two colours (black and white). However, the wheel marking 28 may change between more colours, such as three, four, five, or more colours. A change in the wheel marking 28 may be detected by tracking rotation of the entire wheel marking 28 as a whole or by detecting a change in colour at one or more positions (fixed relative to the optical camera system 14 or the at least one tracking element 20) along the wheel marking 28.

FIG. 4D shows a fourth example of a wheel marking 28 with three optically detectable characteristics 30A-C that each have a different colour. For example, the first characteristic 30A may be red, the second characteristic 30B may be blue, and the third characteristic 30C may be green. The wheel marking 28 may comprise any other number of characteristics 30, such as two, four, five, six, or more. The different colours allow easier tracking of the individual characteristics 30A-C and provide an optically asymmetric appearance that improves accuracy for tracking the wheel marking 28 as a single unit.

In general, the wheel marking 28 may comprise at least an optically detectable first characteristic (e.g., 30A in FIG. 4D) and an optically detectable second characteristic (e.g., 30B in FIG. 4D) which are offset relative to each other in the circumferential direction of the input wheel 22. The first and second characteristics (e.g., 30A and 30B) are different from each other and may in general comprise at least one of different colours and different geometric shapes, as will now be discussed in greater detail with reference to FIGS. 4E to 4G.

FIG. 4E shows another example of a wheel marking 28 with nine optically detectable characteristics 30 that have three different colours. The three colours may be arranged in a sequence that repeats itself in a rotation direction of the input wheel 22 as depicted in FIG. 4E. As a result, a rotation direction of the wheel marking 28 may be determined based on a sequence of colours detected at one or more positions along the wheel marking 28. Alternatively, the wheel marking 28 may not comprise a repeating sequence of colours in order to have an optically asymmetric appearance.

FIG. 4F shows a further example of a wheel marking 28 comprising four optically detectable characteristics 30 that cover essentially an entire side face of the input wheel 22. As a result, there are no or almost no gaps 31 between two characteristics Evidently, the number of such characteristics 30 may be less (e.g., two or three) or more than four.

FIG. 4G shows a still further example of a wheel marking 28 comprising optically detectable characteristics 30 that differ by shape. In the example depicted in FIG. 4G, the optically detectable characteristics 30 have the same colour. Alternatively, at least one of the optically detectable characteristics 30 may have a different colour. Each characteristic 30 may have a single element (e.g., a cross as depicted at the top of FIG. 4G) or multiple elements (e.g., an assembly of dots as depicted at the bottom of FIG. 4G).

Figures 5A, 5B, 5C:
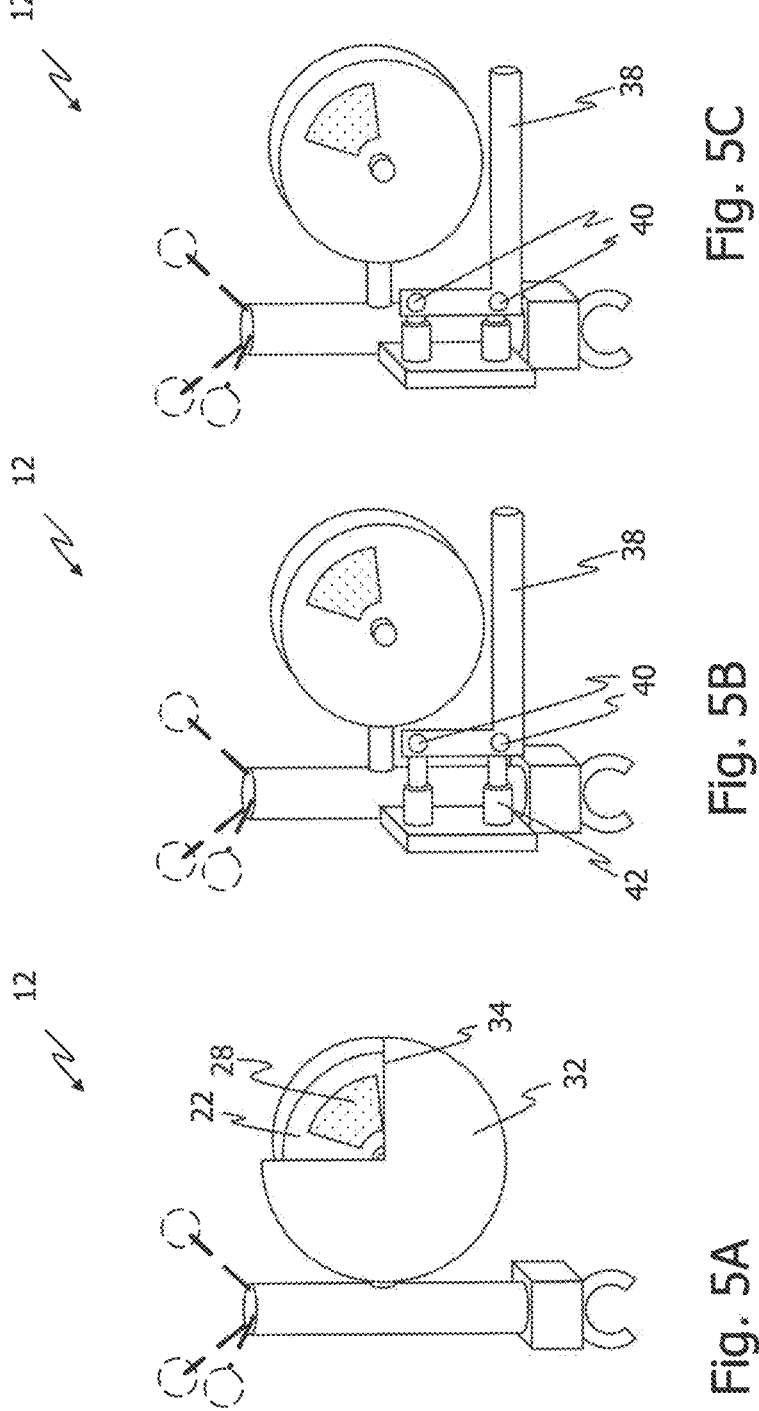
FIG. 5A shows a further example of a surgical input device with an occlusion element.
FIGS. 5B-C show a further example of a surgical input device with an input button in different positions.

FIG. 5A shows another example of the surgical input device 12. This example differs from ones depicted in FIG. 2A and FIG. 2E essentially in the provision of an additional occlusion element 32 configured to cover of a portion of a rotational trajectory of the wheel marking 28. It should be noted that in the present and other examples of the surgical input device 12, one or more tracking elements 20 may or may not be present depending on whether or not the surgical input element 12 is to operate as a surgical tracker. For this reason, the tracking elements 20 are sometimes indicated by dashed lines, but it is to be noted that tracking elements 20 may also be provided in examples in which they are not explicitly indicated.

In the example shown in FIG. 5A, the occlusion element 32 covers approximately 75% of the rotational trajectory of the wheel marking 28. Alternatively, the occlusion element 32 may cover more or less of the rotational trajectory of the wheel marking 28 (e.g., more than 10%, 25%, 50%, 66%, or more than 87.5%). As such, the occlusion element 32 comprises at least one opening 34 (e.g., a recess) where the rotational trajectory of the wheel marking 28 is not covered. Alternatively or additionally, the occlusion element 32 may have a corresponding opening in any other form (e.g., a circular opening).

Since the occlusion element 32 covers a portion of a rotational trajectory of the wheel marking 28, a portion of the wheel marking 28 or the entire wheel marking is covered (and therefore not visible) in certain rotational states of the input wheel 22. As a result, the change of the wheel marking 28 as determined in step 104 of FIG. 3 may be at least partially determined based on a sequence of visible portions of the wheel marking 28. For example, the wheel marking 28 may have optically detectable characteristics 30 with only two different colours (such as the example depicted in FIG. 4F, but with two instead of four colours). During rotation of the input wheel 22, a first and second one of the two colours is alternatingly visible in the opening 34. The colour change itself indicates that there is rotation of the input wheel 22. A rate of the colour change indicates a rotation speed of the input wheel 22.

The occlusion element 32 thus facilitates the determining step 104 in that only a predefined colour change in the field of view of the optical camera system 14 has to be detected to determine a rotation of the input wheel 22. In the absence of the occlusion element 32, more sophisticated image processing algorithms are required in step 104. Therefore, the colour change, and optionally the rate of the colour change, already form a sufficient basis for determining a user input in step 106. For example, for scrolling through a set of pages that loop back to the beginning, the ability to scroll only in one direction still gives access to all pages.

The direction of rotation can be determined based on a sequence of one or more characteristics 30 not being covered by the occlusion element (e.g., being visible in the opening 34). In case the wheel marking comprises one or two optically detectable characteristics 30 offset relative to each other in the circumferential direction of the input wheel 22, the direction of rotation can be determined by analyzing if the characteristics change in an upward or downward manner within a local (stationary) coordinate system.

Determination of the direction of rotation can be facilitated if the wheel marking 28 has three or more optically detectable characteristics 30 offset relative to each other in the circumferential direction of the input wheel 22, wherein at least a first, second and third characteristic 30 are different from each other. Examples of such wheel markings 28 are depicted in FIGS. 4D to 4G and will be exemplarily described with reference to FIG. 4D.

The wheel marking 28 depicted in FIG. 4D comprises a first characteristic 30A, a second characteristic 30B, and a third characteristic 30C. As explained above, the first, second and third characteristics 30A, B, C are different from each other. The characteristics 30A, B, C pass the opening 34 in different sequences that depend on the rotation direction of the input wheel 22. In the case the input wheel 22 depicted in FIG. 4D is rotated clockwise, the characteristics 30A, B, C appear in a first sequence such as the second characteristic 30B, the first characteristic 30A, the third characteristic 30C, and so on (assuming that the second characteristic 30B appears in the opening 34 first). In the case the input wheel 22 depicted in FIG. 4D is rotated counter-clockwise, the characteristic 30A, B, C appear in a second sequence such as the second characteristic 30B, the third characteristic 30C, the first characteristic 30A, and so on (assuming that the second characteristic 30B appears in the opening 34 first). Regardless of the starting point, the first sequence and the second sequence are different. Therefore, the rotation direction can be determined from a single transition from one of the three characteristics 30A, B, C to a different one of the three characteristics 30A, B, C.

The opening 34 may be dimensioned at least essentially in the same size or smaller than one of the first, second, etc. characteristics 30. As a result, only one characteristic 30 is visible when aligned with the opening 34, which increases the accuracy of determining a particular sequence of characteristics 30. Alternatively, the opening 34 may be dimensioned larger than the characteristics 30. A larger view of the wheel marking trajectory increases the time for capturing characteristics 30 by the optical camera system 14 and therefore increases detection accuracy of characteristics at larger rotation speeds.

As has been explained above, the input wheel 22 allows for a scroll wheel-type input similar to the scroll wheel of a computer mouse. The surgical input device 12 may further comprise a mechanism that additionally allows for a mouse click type input, as will now be described with reference to FIG. 5B and FIG. 5C. The surgical input device of FIG. 5B and FIG. 5C essentially differs from the examples depicted in FIG. 2B and FIG. 2E in the provision of an additional input button 38.

In the example of FIG. 5B, the input button 38 comprises a piston-type push rod configured for a guided translatory movement against one or more spring elements biasing the input button towards the right hand side in FIG. 5B. In the example of FIG. 5B, one respective spring element (not shown) is received in each of two cylinders 42. Each spring element is arranged between a bottom of the respective cylinder 42 and a protrusion of the input button 38 extending into the respective cylinder 42. Of course, the number of cylinders 42 and protrusions may vary, and also alternative mechanisms for guiding a translatory movement of the input button 38 may be implemented.

Upon the user 8 pressing with a finger against the free end of the input button 38, the input button 38 is moved in a translatory manner from a first position (see FIG. 5B) to a second position (see FIG. 5C) against the spring bias provided by the spring elements in the cylinders 42. The input button 38 returns to the first position upon the user 8 removing the pressure from the input button 38. In this way, a click-type user input (e.g., for confirmation purposes) can be realized.

A transition of the input button 38 between the first position and the second position is optically detectable. To this end, the input button 38 comprises an optically detectable button-related marking 40 (here: two coloured circles). The button-related marking 40 moves with the input button 38 between the first position and second position. Therefore, the corresponding transition of the input button 38 can be detected by detecting movement of the button-related marking 40. The button-related marking 40 may be detected by the optical camera system 14 or by a tracking camera system.

In other variants, the input button 38 may not be spring-biased. In such a case, the user can transition the input button 38 between the first and the at least one second position by pushing or pulling the input button 38.

Figure 5E:
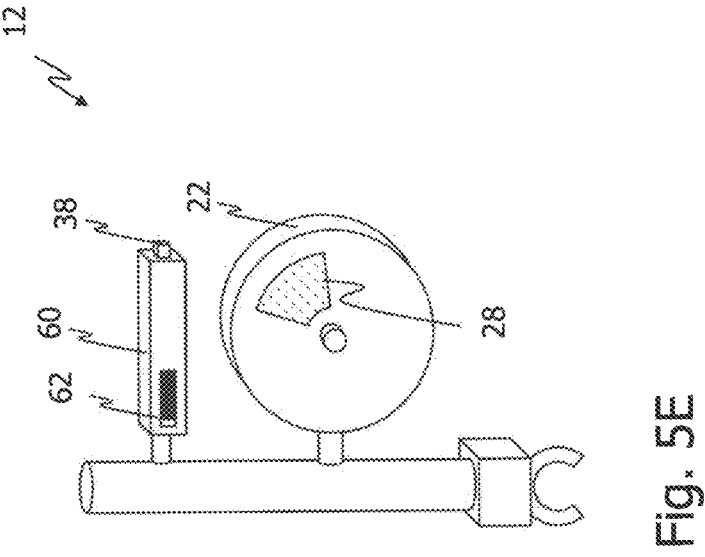
FIGS. 5D-E show a still further example of a surgical input device with an input button in different positions.
Figure 5D:
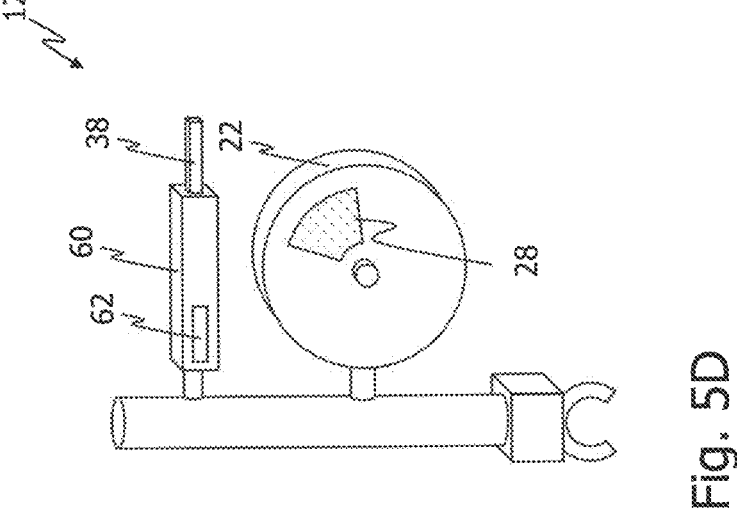

FIG. 5D and FIG. 5E illustrate a further exemplary realization of the input button 38. Here, the input button 38 is movable in a translatory manner within a housing 60 having a window 62. The input button 38 has a first end guided within the housing 60 and a second end extending out of the housing 60. A spring element (not shown) is arranged to bias the input button 38 towards the outside of the housing 60, as illustrated in FIG. 5D. When the user 8 presses the input button 38 against the spring bias into the housing 60, as illustrated in FIG. 5E, a coloured end of the input button 38 aligns with the window 62 in the housing. The resulting visibility of the coloured end of the input button 38 to the optical camera system 14 (or a tracking camera system) will thus indicate a user input, i.e., actuation of the input button 38. In some variants, the length of the coloured end visible in the window 62 can be evaluated as an indication of the degree to which the input button 38 has been pressed.

In the examples illustrated in FIGS. 5B to 5E, the input wheel 22 and the input button 38 are provided in combination, for example to allow for a parameter selection via the input wheel 22 followed by a confirmation of the selected parameter via the input button 38. The input wheel 22 may be omitted in examples of the surgical input device 12 in which the input button 38 is present, for example to allow only click-type input operations such as confirmations.

Figure 6B:
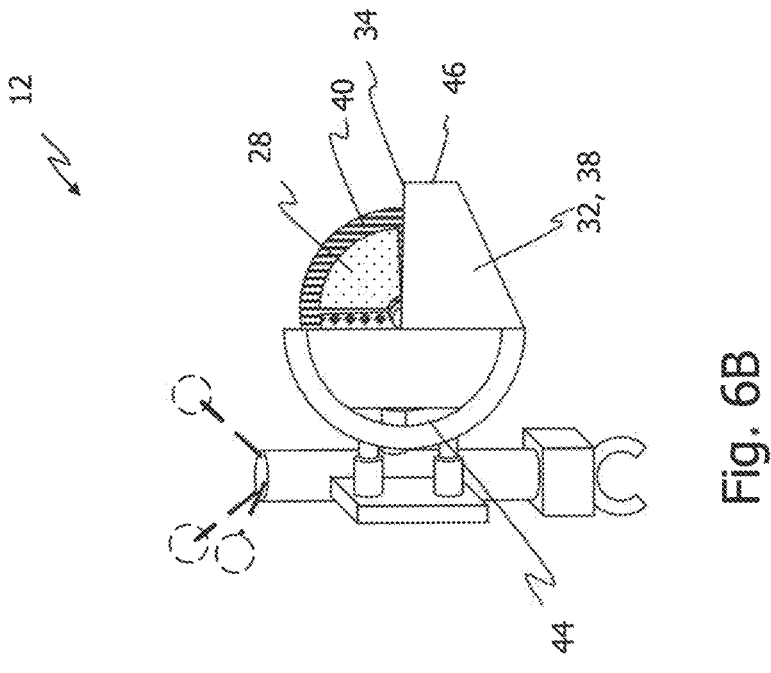
FIG. 6B shows the surgical input device of FIG. 6A, wherein the input button is in a second position.
Figure 6A:
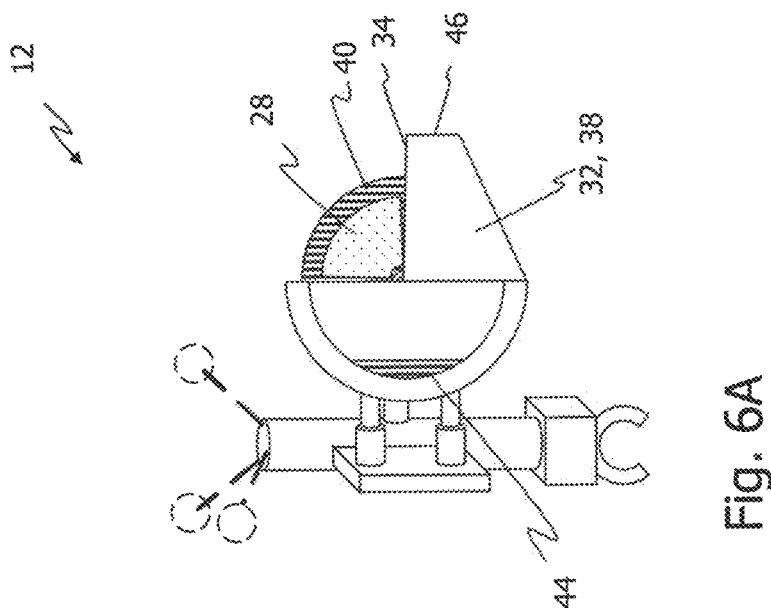
FIG. 6A shows another example of a surgical input device with an input button in a first position.

FIG. 6A shows a still further example of a surgical input device 12 that essentially comprises a combination of an input wheel 22 with an associated occlusion element 32 and an input button 38. In this example, the surgical input device 12 has an input button 38 that also functions as (e.g., is integrated with) or is coupled to the occlusion element 32. One may also say that the occlusion element 32 acts as the input button 38. The input button 38 is movable between a first position and a second position, wherein FIG. 6A shows the input button 38 in the first position. Movement of the input button 38 is guided in a translatory manner, for example as explained with reference to FIGS. 5B and 5C. Moreover, the input button 38 may be spring-biased into the first position, as also explained above.

As illustrated in FIG. 6A, the input wheel 22 comprises both a wheel marking 28 and an optically detectable button-related marking 40. The button-related marking 40 is not arranged on a rotational trajectory of the wheel marking 28.

In the example shown in FIG. 6A, the button-related marking 40 is arranged at a radially outer edge of a side face of the input wheel 22. The push button 38 further comprises an opening 44 (configured as a recess in the occlusion element 32) through which the button-related marking 40 is visible when the push button 38 is in the first position. The button-related marking 40 does not change in the circumferential direction of the input wheel 22. Therefore, when the push button 38 is in the first position, the button-related marking 40 is visible through the opening 44 and does not (or at least not significantly) change as the input wheel 22 is rotated. For example, the button-related marking 40 may have a yellow colour. During rotation of the input wheel 22, the opening 44 always gives a view on the yellow colour of the button-related marking 40, whereas the wheel marking 28 visible through the other opening 34 changes as explained above with reference to FIGS. 4C to 4G (e.g., in colour and/or shape).

FIG. 6B shows the input device 12 of FIG. 6A when the input button 38 has been brought into in the second position, for example by applying a force by a user's finger on a face 46 of the input button 38. In the second position, the opening 44 is brought out of alignment with the button-related marking 40. In the example shown in FIG. 6B, the opening 44 is located offset relative to the input wheel 22 in such a way that the opening 44 provides a view past the input wheel 22. As a result, the button-related marking 40 is not (or at least significantly less) visible in the opening 44. Therefore, the user 8 can selectively cause the button-related marking 40 to be visible or not visible by moving the input button 38 between the first and the second positions.

The visibility of the button-related marking 40 in any of the above examples can be used to manually issue further or alternative user input compared with the user input determined in step 106 of FIG. 3. The method illustrated in FIG. 3 may thus comprise a further step (not shown) of determining, based on the image data received in step 102 or based on different image data, a transition of the input button 38 between the first position and the second position (e.g., from the first position to the second position or vice versa). Determining the transition may comprise determining that a visibility of the button-related marking 40 in the opening 44 changes. For example, the button-related marking 40 may have a yellow colour. Therefore, the opening 44 gives a view on yellow colour when the input button 38 is in the first position. When the input button 38 is moved to the second position, the opening 44 does not give a view on yellow colour. Therefore, determining that the second opening 44 switches from yellow to a non-yellow view allows determining a transition from the first position to the second position. Of course, the colour yellow has been used only for illustrative purposes. Moreover, a different colour or shape may be visible in the second position.

A transition of the input button 38 may be determined in different ways. In the example shown in FIG. 5B and FIG. 5C, a transition of the input button 38 from the first position to the second position may be determined based on button-related marking 40 moving to the left (e.g., relative to a certain reference such as the surgical object or, if present, the one or more tracking elements, or after a movement derived from tracking information has been subtracted). The method illustrated in FIG. 3 may then further comprise determining a user input associated with the determined transition of the input button 38 between the first position and the second position.

In the above variants, the user input is associated with a transition between the first position and the second position (i.e., a transition between only two positions, which may be two opposite end positions of the input button 38). Such a binary selection of one or two states can be interpreted as a command related to a confirmation or a selection. The user input via the input button 38 may therefore be related to any action that can be performed by a mouse click.

In other variants, the user input via the input button 38 may be associated with a transition between more than two positions (including a continuous transition). For example, the user input may be interpreted as a command that is scaled proportional to a degree of movement of the input button 38 (e.g., proportional to a distance moved or proportional to a number of positions passed by the input button 38).

Figure 7B:
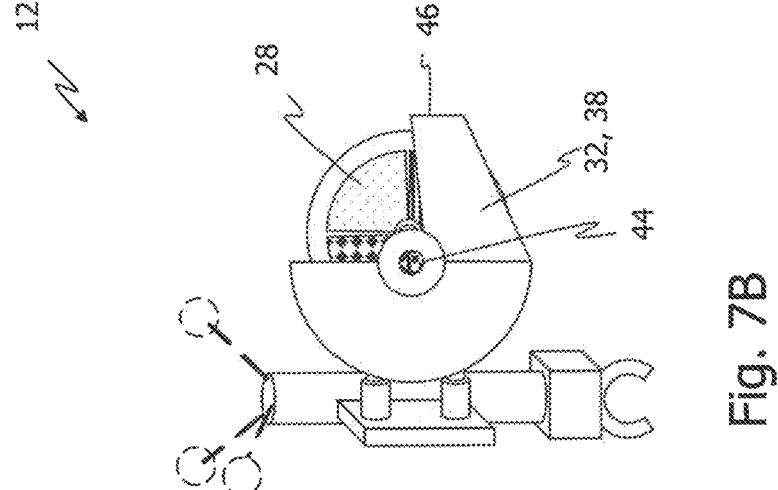
FIG. 7B shows the surgical input device of FIG. 7A, wherein the input button is in a second position.
Figure 7A:
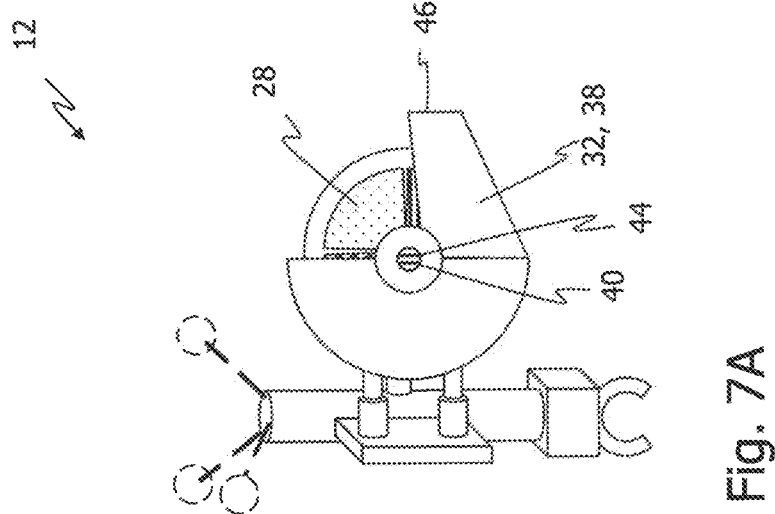
FIG. 7A shows a still further example of a surgical input device with an input button in a first position.

The button-related marking 40 depicted in FIGS. 6A and 6B is arranged on a radially outer edge of a side face of the input wheel 22 and does not overlap with the circular trajectory of the wheel marking 28. Alternatively or additionally, the button-related marking 40 may be located radially inward of the wheel marking 28. FIG. 7A shows a corresponding example of the surgical input device 12, which essentially differs from the example depicted in FIG. 6A in that the button-related marking 40 and the opening 44 are located at a hub of the input wheel 22 when the input button 38 is at the first position. FIG. 7B shows the surgical input device 12 of FIG. 7A when the input button 38 is in the second position. As a result, the opening 44 is out of alignment with the button-related marking 40. Instead, the wheel marking 28 can be seen in the opening 44. In order to improve detection of a transition of the input button 38, the wheel marking 28 may have characteristics that optically differ from the button-related marking 40.

The user 8 may wish to conveniently use the input wheel 22 and the input button 38 in tandem. For example, the user 8 may wish to use the input wheel 22 to scroll through a selection of menu items and then use the input button 38 to select one of the items. The input button 38 and the input wheel 22 may thus be arranged relative to each other so as to permit a one-hand operation of both the input button 38 and the input wheel 22. To this end, the input button 38 may be arranged adjacent to the input wheel 22. The input button 38 may have a face 46 configured to be pressed by a finger, wherein the face 46 projects relative to a wheel engagement surface of the input wheel 22 in the first position and the second position of the input button 38. As a result, the user 8 can use a certain finger (such as the thumb) to selectively rotate the input wheel 22 or push the input button 38 from the first into the second position without abutting against the input wheel 22.

Figures 8A, 8B, 8C, 8D:
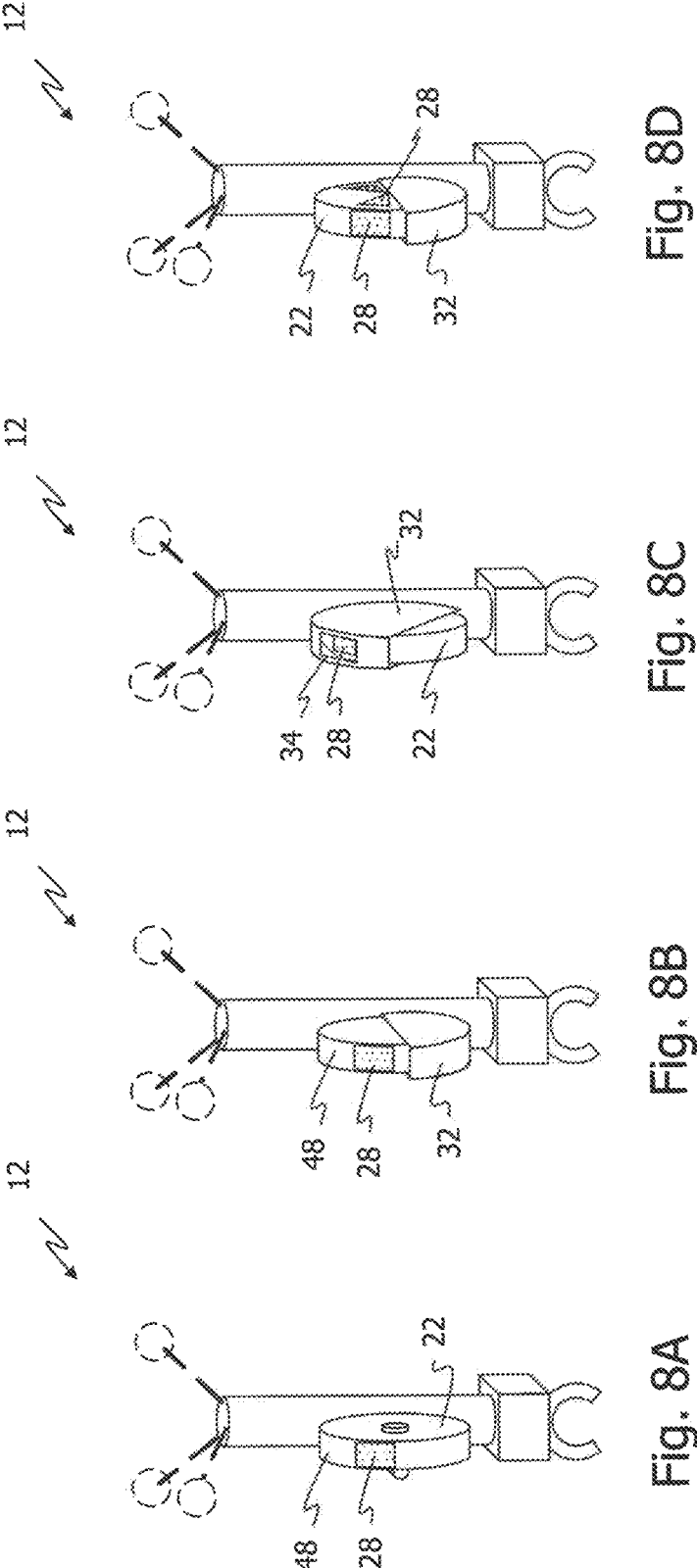
FIGS. 8A-D show further examples of the surgical input device with exemplary placements of wheel markings.

The surgical input devices 12 of FIGS. 2A to 7B have a wheel marking 28 arranged on a side face of the input wheel 22. Alternatively or additionally, the wheel marking 28 may at least partly be arranged on an outer rim surface 48 of the input wheel 22 (i.e. the "tread" of the input wheel 22). FIG. 8A shows a corresponding example of the surgical input device 12, which essentially differs from the example shown in FIG. 2A in that the wheel marking 28 is arranged on the outer rim surface 48 of the input wheel 22.

FIG. 8B shows another example of the surgical input device 12 similar to FIG. 8A but with an additional occlusion element 32. The occlusion element 32 depicted in FIG. 8B covers part of both, the outer rim surface 48 and the side surface of the input wheel 22. Alternatively, the occlusion element 32 may only cover either the outer rim surface 48 or the side surface of the input wheel 22.

FIG. 8C shows a further example of the surgical input device 12, wherein the occlusion element 32 has an opening 34 in a region of the rim surface 48.

FIG. 8D shows a still further example of the surgical input device 12, wherein the wheel marking 28 is arranged on the outer rim surface 48 of the input wheel 22 and on a side face of the input wheel 22. The wheel marking 28 may generally be arranged on one or both sides of the input wheel 22.

As has become apparent from the above description of various examples, the surgical input device 12 described herein includes a rotatable input wheel 22 with an optically detectable wheel marking 28, which enables manual user input to a remote computing system 18 that may be communicatively coupled to an optical camera system 14. The surgical input device 12 can in some variants be realized as a fully passive tool that does not consume any electric power.

The interface 24 allows the surgical input device 12 to be attached to a surgical object (e.g., a patient or a surgical instrument) in a sterile environment. Since the surgical input device 12 is located in a sterile environment and at the surgery site, the user 8 can issue commands without having to walk or turn to conventional input devices of the computing system 18. The user 8 does not have to disinfect hands, as the surgical input device 12 is sterile. Therefore, the surgical procedure can be carried out faster and more efficiently.

With the surgical input device 12 attached to a surgical object such as a surgical tracker, the user 8 does not have to hold or retrieve the surgical input device 12 as a separate component in order to issue a user input. As such, no "free hand" is needed for performing a user input, which also increases efficiency of the surgical procedure.

The wheel marking 28 and the button-related marking 40 can be realized as passive markers. Furthermore, changing the wheel marking 28 and button-related marking can also be realized mechanically and therefore does not require electrical components. As a result, the surgical input device 12 is more light weight and less complex.

The features described in relation to the exemplary embodiments shown in the drawings can be readily combined to result in different embodiments. It is apparent, therefore, that the present disclosure may be varied in many ways. Such variations are not to be regarded as a departure from the scope of the present disclosure.

The following numbered examples are also encompassed by the present disclosure and may fully or partly be incorporated into embodiments.

1. A surgical input device configured to enable manual user input to a remote computing system, the surgical input device comprising an interface configured to be attachable to a surgical object; and a manually operable input wheel infinitely rotatable relative to the interface, wherein the input wheel defines an optically detectable wheel marking.

2. The surgical input device according to example 1, wherein the wheel marking changes in a circumferential direction of the input wheel.

3. The surgical input device according to any of the preceding examples, wherein the wheel marking comprises at least an optically detectable first characteristic and an optically detectable second characteristic which are offset relative to each other in the circumferential direction of the input wheel, wherein the first and second characteristics are different from each other.

4. The surgical input device according to example 3, wherein the first and second characteristics comprise at least one of different colours and different geometric shapes.

5. The surgical input device according to any of the preceding examples, further comprising an occlusion element configured to cover a portion of a rotational trajectory of the wheel marking.

6. The surgical input device according to example 5 when depending at least on example 3, wherein the occlusion element has a first opening that is dimensioned at least essentially in the same size or smaller than one of the first and second characteristics.

7. The surgical input device according to any of the preceding examples, further comprising a manually operable input button movable between a first position and at least one second position, wherein a transition of the input button between the first position and the at least one second position is optically detectable.

8. The surgical input device according to example 7, further comprising an optically detectable button-related marking, wherein the transition between the first position and the at least one second or a third position changes an optical visibility of the button-related marking.

9. The surgical input device according to example 7 or 8 when depending at least on example 5, wherein the occlusion element is movable with the input button.

10. The surgical input device according to examples 8 and 9, wherein the occlusion element has a second opening that, upon the transition between the first position and the at least one second or third position, can selectively be brought in and out of alignment with the button-related marking.

11. The surgical input device according to any of the examples 7 to 10, wherein the input button and the input wheel are arranged relative to each other so as to permit a one-hand operation of both the input button and the input wheel.

12. The surgical input device according to any of the preceding examples, wherein the wheel marking is arranged on at least one of a side face of the input wheel and an outer rim surface of the input wheel.

13. The surgical input device according to any of the preceding examples, wherein rotatability of the input wheel is divided into discrete increments.

14. The surgical input device according to any of the preceding examples, further comprising at least one tracking element configured to be detectable by a tracking system.

15. A surgical input system comprising the surgical input device according to any of the examples 1 to 14; and an optical camera system configured to generate image data representative of at least the wheel marking.

16. A method for determining a manual user input at a surgical input device to a remote computing system, wherein the surgical input device is attached to a surgical object and comprises a manually operable input wheel that is infinitely rotatable relative to the surgical object, wherein the input wheel defines an optically detectable wheel marking, the method being implemented by at least one processor and comprising receiving first image data representative of the wheel marking;

determining, based on the first image data, a change of the wheel marking caused by rotation of the input wheel; and determining a first user input associated with the change of the wheel marking.

17. The method according to example 16, further comprising interpreting the first user input as a command that is related to at least one of (i) an incrementation or a decrementation of a parameter;
(ii) a mode change; and
(iii) a user confirmation.

18. The method according to example 16 or 17, wherein the wheel marking comprises an optically detectable first characteristic, an optically detectable second characteristic, and an optically detectable third characteristic which are offset relative to each other in the circumferential direction of the input wheel, wherein the first, second and third characteristics are different from each other, and wherein the marker further comprises an occlusion element configured to cover of a portion of a rotational trajectory of the wheel marking; and wherein determining the change of the wheel marking comprises determining a sequence of the first, second and third characteristics not being covered by the occlusion element.

19. The method according to any of the examples 16 to 18, wherein the surgical tracker further comprises a manually operable input button that is movable between a first position and at least one second position, and wherein the method further comprises determining, based on the first image data or based on second image data, a transition of the input button between the first position and the at least one second or a third position; and determining the first or a second user input associated with the determined transition.

A computer program product, comprising instructions that, when executed on at least one processor, cause the at least one processor to carry out the method according to any of examples 16 to 19.

The invention claimed is:

1. A surgical input device attachable or attached to a surgical object and configured to enable manual user input to a remote computing system, the surgical input device comprising:

a manually operable input wheel configured to be rotated, wherein the input wheel defines an optically detectable wheel marking;

a manually operable input button movable between a first position and at least one second position;

an optically detectable button-related marking; and an occlusion element configured to cover a portion of a rotational trajectory of the wheel marking, wherein a transition of the input button between the first position and the at least one second position is optically detectable in that the transition changes an optical visibility of the button-related marking.

2. The surgical input device according to claim 1, wherein the wheel marking changes in a circumferential direction of the input wheel.

3. The surgical input device according to claim 2, wherein the wheel marking comprises at least an optically detectable first characteristic and an optically detectable second characteristic which are offset relative to each other in the circumferential direction of the input wheel, wherein the first and second characteristics are different from each other.

4. The surgical input device according to claim 3, wherein the first and second characteristics comprise different colours.

5. The surgical input device according to claim 3, wherein the first and second characteristics comprise different geometric shapes.

6. The surgical input device according to claim 3, further comprising an occlusion element configured to cover a portion of a rotational trajectory of the wheel marking, wherein the occlusion element has a first opening that is dimensioned at least essentially in the same size or smaller than one of the first and second characteristics.

7. The surgical input device according to claim 6, wherein the occlusion element is movable with the input button.

8. The surgical input device according to claim 6, wherein the occlusion element has a second opening that, upon the transition between the first position and the at least one second position, can selectively be brought in and out of alignment with the button-related marking.

9. The surgical input device according to claim 1, wherein the occlusion element is movable with the input button.

10. The surgical input device according to claim 1, further comprising an interface configured to be attachable or attached to the surgical object.

11. The surgical input device according to claim 1, wherein the input button and the input wheel are arranged relative to each other so as to permit a one-hand operation of both the input button and the input wheel.

12. The surgical input device according to claim 1, wherein the wheel marking is arranged on at least one of a side face of the input wheel and an outer rim surface of the input wheel.

13. The surgical input device according to claim 1, wherein rotatability of the input wheel is divided into discrete increments.

14. The surgical input device according to claim 1, further comprising at least one tracking element configured to be detectable by a tracking system.

15. A method for determining a manual user input at a surgical input device to a remote computing system, wherein the surgical input device is attached to a surgical object and comprises a manually operable input wheel that is rotatable relative to the surgical object, wherein the input wheel defines an optically detectable wheel marking configured to be detectable by an optical camera, and wherein the surgical input device further comprises a manually operable input button that is movable between a first position and at least one second position, the method being implemented by at least one processor and comprising receiving first image data representative of the wheel marking;

determining, based on the first image data, the wheel marking;

determining a first user input associated with the wheel marking;

determining, based on the first image data or based on second image data, a transition of the input button between the first position and the at least one second position; and determining the first or a second user input associated with the determined transition.

16. The method according to claim 15, further comprising interpreting the first user input as a command that is related to at least one of (i) an incrementation or a decrementation of a parameter;

(ii) a mode change; and (iii) a user confirmation.

17. The method according to claim 15, wherein the steps of determining, based on the first image data, the wheel marking and determining the first user input associated with the wheel marking comprises:

determining, based on the first image data, a change of the wheel marking caused by rotation of the input wheel; and determining the first user input associated with the change of the wheel marking.

18. The method according to claim 17, wherein the wheel marking comprises an optically detectable first characteristic, an optically detectable second characteristic, and an optically detectable third characteristic which are offset relative to each other in a circumferential direction of the input wheel, wherein the first, second and third characteristics are different from each other, and wherein the marker further comprises an occlusion element configured to cover of a portion of a rotational trajectory of the wheel marking; and wherein determining the change of the wheel marking comprises determining a sequence of the first, second and third characteristics not being covered by the occlusion element.

19. A computer program product, comprising instructions stored on at least one non-transitory computer readable medium that, when executed on at least one processor, cause the at least one processor to carry out a method for determining a manual user input at a surgical input device to a remote computing system, wherein the surgical input device is attached to a surgical object and comprises a manually operable input wheel that is rotatable relative to the surgical object, wherein the input wheel defines an optically detectable wheel marking configured to be detectable by an optical camera, and wherein the surgical input device further comprises a manually operable input button that is movable between a first position and at least one second position, the method comprising receiving first image data representative of the wheel marking;

determining, based on the first image data, the wheel marking;

determining a first user input associated with the wheel marking;

determining, based on the first image data or based on second image data, a transition of the input button between the first position and the at least one second position; and determining the first or a second user input associated with the determined transition.

* * * * *